(12) United States Patent
Knight (10) Patent No.: US 11,589,844 B2
(45) Date of Patent: Feb. 28, 2023

(54) INFANT URINE COLLECTOR

(71) Applicant: Med-Knight Enterprises, LLC, Tampa, FL (US)

(72) Inventor: Julie Knight, Tampa, FL (US)

(*) Notice: Subject to any disclaimer, the term of this patent is extended or adjusted under 35 U.S.C. 154(b) by 302 days.

(21) Appl. No.: 16/847,720

(22) Filed: Apr. 14, 2020

(65) Prior Publication Data
US 2020/0330079 A1 Oct. 22, 2020

Related U.S. Application Data

(60) Provisional application No. 62/834,424, filed on Apr. 16, 2019.

(51) Int. Cl.
| | | |
|---|---|---|
| *A61B 10/00* | (2006.01) | |
| *A61F 5/451* | (2006.01) | |
| *A61F 5/44* | (2006.01) | |
| *A61F 5/443* | (2006.01) | |

(52) U.S. Cl.
CPC ............ *A61B 10/007* (2013.01); *A61F 5/443* (2013.01); *A61F 5/4405* (2013.01); *A61F 5/451* (2013.01); *A61B 2503/045* (2013.01)

(58) Field of Classification Search
CPC ....... A61B 10/007; A61B 5/00; A61F 5/4405; A61F 5/451
See application file for complete search history.

(56) References Cited

U.S. PATENT DOCUMENTS

| | | | | |
|---|---|---|---|---|
| 2,277,043 | A * | 3/1942 | Cohn ..................... | A61F 5/451 604/348 |
| 2,920,625 | A * | 1/1960 | Green ..................... | A61F 5/451 604/348 |
| 3,532,093 | A * | 10/1970 | Lovret .................... | A61F 5/451 604/350 |
| 4,064,760 | A * | 12/1977 | Benjamin ............ | A61B 10/007 73/863.52 |
| 11,135,104 | B2 * | 10/2021 | Barnhorst ............. | A61F 13/495 |
| 2007/0185466 | A1 * | 8/2007 | Co ........................ | A61B 10/007 604/385.19 |

\* cited by examiner

*Primary Examiner* — Benjamin J Klein
*Assistant Examiner* — Hans Kaliher
(74) *Attorney, Agent, or Firm* — Larson & Larson; Justin P. Miller; Frank Liebenow (57) ABSTRACT

The urine collection insert, or infant urine collector, is an insert for placement inside a typical diaper. Placement of the insertion preferably occurs with the first diapering after birth. The infant's urine is channeled into a portal, through a one-way valve, and into a reservoir. Coincident with the next diaper change, the insert is collected and the urine withdrawn for testing. Throughout the process, all chain-of-custody requirements being followed. The design of the urine collection insert prevents contamination from the infant's feces, most likely to be meconium—the feces of a newborn formed from epithelial cells, lanugo (hair), mucus, amniotic fluid, bile, and water. By avoiding contamination, the integrity of the sample will be maintained and accuracy of results increased, whether positive or negative.

2 Claims, 15 Drawing Sheets

INFANT URINE COLLECTOR

CROSS-REFERENCE TO RELATED APPLICATION

This application is a continuation-in-part of U.S. Pat. App. Ser. No. 62/834,424, filed Apr. 16, 2019, titled Infant Urine Collector.

FIELD

This invention relates to the field of diagnostic fluid collection and more particularly to a device for the collection of urine from infants, particularly newborns.

BACKGROUND

The opioid crisis has caused compilations that ripple beyond adult addiction. When a pregnant mother uses opioids, or other substances including alcohol or cocaine, the baby is born with his or her own addiction and therefore, anticipated withdrawal.

Treatment options exist for babies born with substance exposure issues, but early diagnosis is critical.

For example, if a newborn was exposed to heroin or cocaine, withdrawal will likely occur within forty-eight hours. Thus, treatment must begin quickly.

But if a newborn was exposed to methadone or benzodiazepines, withdrawal may be delayed as long as two weeks. Without early diagnosis, the infant has likely left the care and supervision of the hospital and been returned to a home where proper care may not be available. Thus, early diagnosis is critical to planning future care.

Current diagnostic methods require drawing blood from the baby. This is not only emotionally traumatic for the baby and parents, but the removal of blood can be taxing on a baby given its limited blood supply due to its small size.

Because the current testing methods require a blood draw, the diagnosis is only performed when there is suspicion that the mother has been abusing or using substances, or when the baby exhibits symptoms of withdrawal. This is an imperfect system, and thus some babies are not tested, and as a result treatment is delayed.

What is needed is a device for easily collecting fluid from a baby for testing purposes.

SUMMARY

The urine collection insert, or infant urine collector, is an insert for placement inside a typical diaper. The infant's urine is channeled into a portal, through a valve, and into a reservoir. The device is intended for insertion into the diaper that is placed on the infant immediately after birth. Coincident with a diaper change, the insert is collected and the urine withdrawn for testing.

The design of the urine collection insert prevents contamination from the infant's feces/stool, most likely to be meconium—the feces of a newborn formed from epithelial cells, lanugo (hair), mucus, amniotic fluid, bile, and water. By avoiding contamination, the accuracy of testing increases.

The urine collection insert is preferably inserted inside a diaper, held in place by an adhesive backing. Alternatively, the urine collection insert is incorporated into a diaper as a single unit. As a further alternate, the urine collection insert is integrated into underwear, allowing for urine collection in older children and adults.

The urine collection insert is substantially flat, with an internal space formed by a front wall and back wall, optionally joined by a perimeter wall. Alternatively, the front wall and back wall are joined at their edges, thus avoiding the need for an additional wall. Alternatively, the back wall, or lower wall, is shaped to form a reservoir that acts to collect the urine.

The upper portion of the insert is a collection section. The genitals of the infant pass through an opening in the collection section, or are in close proximity to the opening. A perimeter seal formed from a non-shedding, non-irritating, and sterile material that forms a seal between the insert and the skin of the infant.

The perimeter seal is preferably formed from a hydrocolloidal material because such a material naturally adheres to skin, thus forming a seal without the need for adhesive. Hydrocolloidal materials contain gel-forming agents in an adhesive compound laminated onto a flexible, water-resistant outer layer, optionally further including an alginate to increase absorption capabilities.

The collection section, primarily formed from the pocket, is constructed from a material that resists collapse, thus ensuring that a space remains for the urine to flow. But the pocket remains sufficiently flexible to allow the device to confirm to the infant and follow the shape of the diaper. Thus, the urine collection insert is optionally hourglass shaped, narrowing at approximately the middle of the insert.

When the infant urinates, the urine flows through the opening, down through a one-way valve, and into a reservoir within the storage section. The urine is maintained in the reservoir until removed for testing. The goal is to collect 5-7 mL of urine.

The one-way valve must be of a type that permits flow even with a low differential pressure. The primary motivating force for the flow of urine through the valve is gravity, with the baby generally on his or her back, the urine flowing from the upper part of the insert around the genitals and down into the reservoir.

The collection section, or bag, is formed from a flexible material. This allows the device to conform to the diaper interior, or the infant's skin diapered area.

Discussing the device generally, the materials are chosen to reduce contamination of the urine, thus ensuring accurate test results. This includes avoiding the use of an absorbent material in the reservoir to avoiding contaminating the urine sample.

The following materials are preferred:
Reservoir: non-irritating, hypoallergenic, nontoxic, flexible light weight plastic: PE (polyethylene), PVC (polyvinyl chloride), PU (polyvinyl chloride)
One-way valve: PVC, PP (polypropylene), PE or PU
Hydrocolloidal material: coated paper with hydrocolloid material
ID tag: coated paper with adhesive to seal
Drain hole cover: non-stick foil or paper
Contamination of the urine sample is both a physical and chemical issue. Physically, particulates may clog the testing equipment. Chemically, additional materials will alter the results of the mass spectrometry testing, and may obscure the presence of substances in the urine sample. For example, obscuring 6-monoacetylmorphine ("6-MAM"), which is a metabolized form of heroin.

While the urine collection insert is important, equally critical is the correct manner of use. Both leaking out of, and contamination into, the device must be prevented.

Before use, a cover is removed from the opening, exposing the perimeter seal. The device is then applied to the infant, whether directly or using a diaper.

Following collection, a cover is removed from the ID tag, which then folds over to fully cover the opening. An adhesive cover is removed to expose an adhesive layer, which then covers the opening and perimeter seal.

The ID tag is preferably larger than the opening, with an adhesive layer. In this manner the opening and perimeter seal are fully covered and enclosed.

The ID tag includes all information relevant to the sample. For example, patient name, identification number, collection date, collection time, and identity of individual performing collection.

The device—sealed, with the sample held within and with the ID tag visible—is now moved to the testing lab. This will allow for proper chain of custody procedures as related to the sample and the infant.

When the sample is ready for removal, the drain hole cover is removed, allowing the sample to be drained and tested.

After removal of the insert from an infant's diaper, the chain of custody must be controlled to avoid intentional or accidental substitution, as well as to prevent tampering.

Given that the opioid crisis has affected individuals across class and income brackets, infants at risk are hard to identify. Thus, collection and analysis of urine should be a standard part of newborn care in every instance, regardless of how unlikely the risk of substance abuse or addiction may be. Such broad testing is supported by the non-invasive nature of the urine collection insert.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Figure 1:
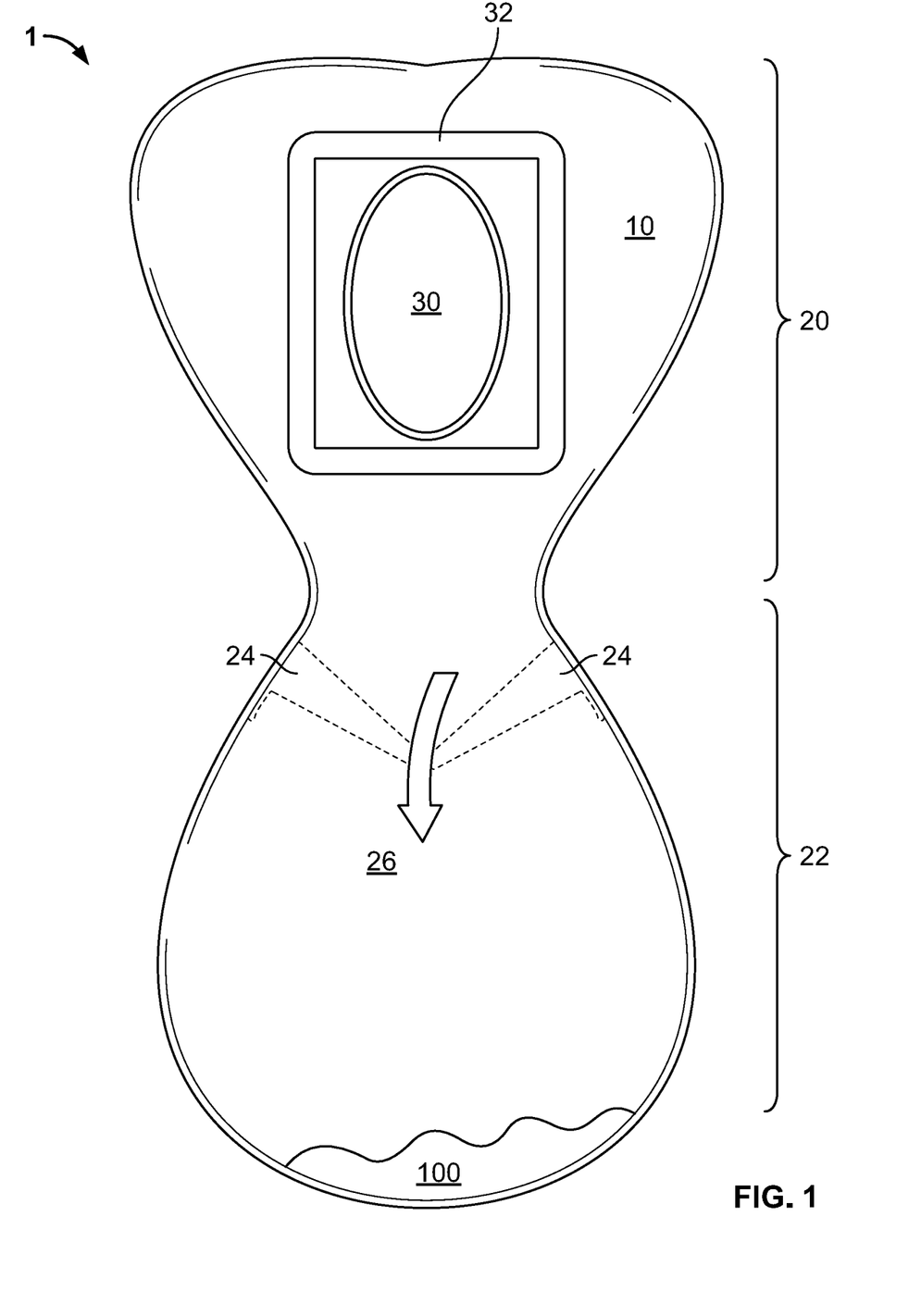
FIG. 1 illustrates a front view of the urine collection insert.
Figure 2:
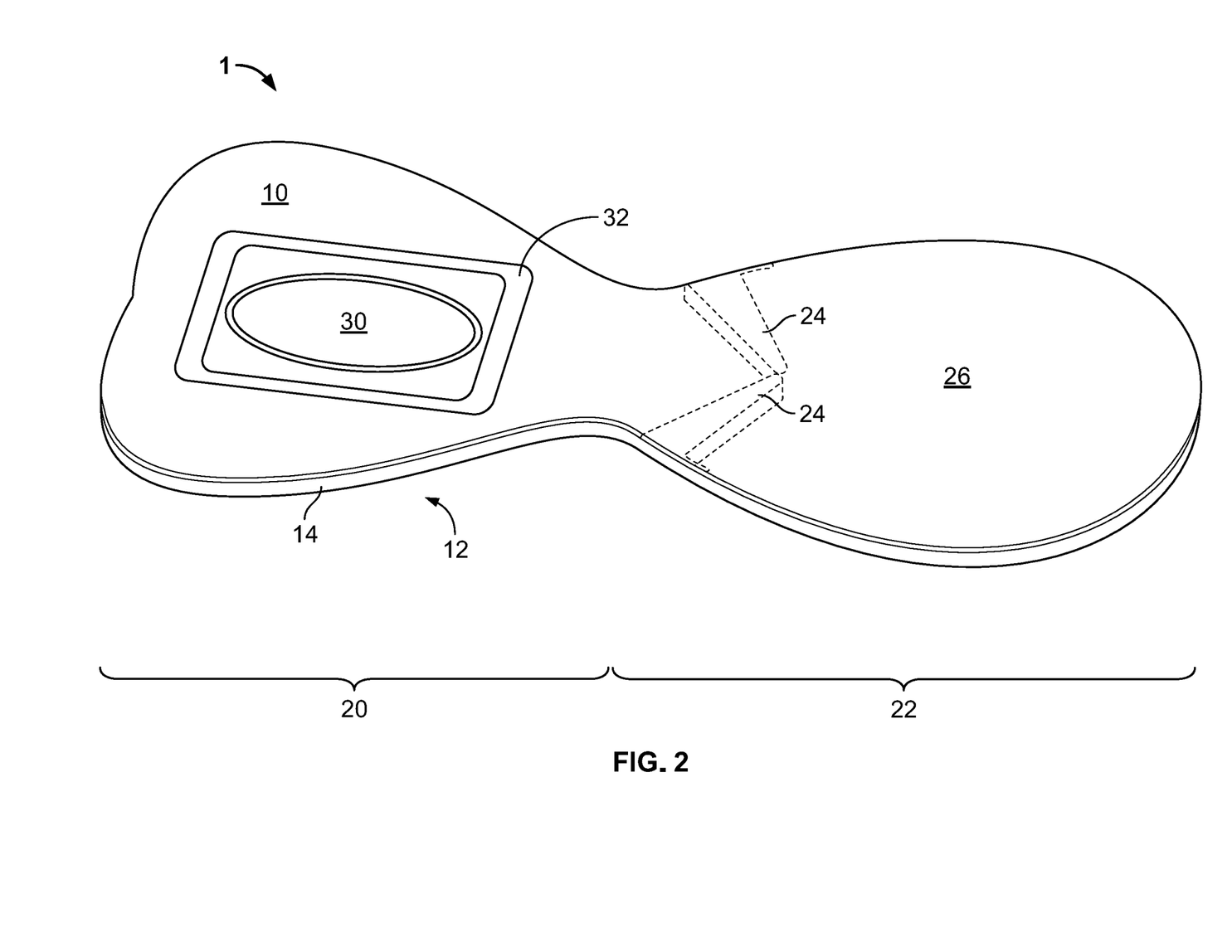
FIG. 2 illustrates an isometric view of the urine collection insert.

Referring to FIGS. 1 and 2, a front view and isometric view of the urine collection insert are shown.

The urine collection insert 1 is formed from a front wall 10 and rear wall 12 joined by an optional perimeter wall 14.

The upper half of the urine collection insert 1 forms the collection section 20, with the lower half forming the storage section 22.

An infant's genitals interface with the opening 30, with urine directed through the opening 30. A perimeter seal 32 substantially seals the urine collection insert 1 to the infant, minimizing leakage.

After the urine 100 enters the opening 30, it flows through the one-way valve 24 and into the reservoir 26. Urine 100 is held in the reservoir 26 in anticipation of future removal and testing.

Figure 3:
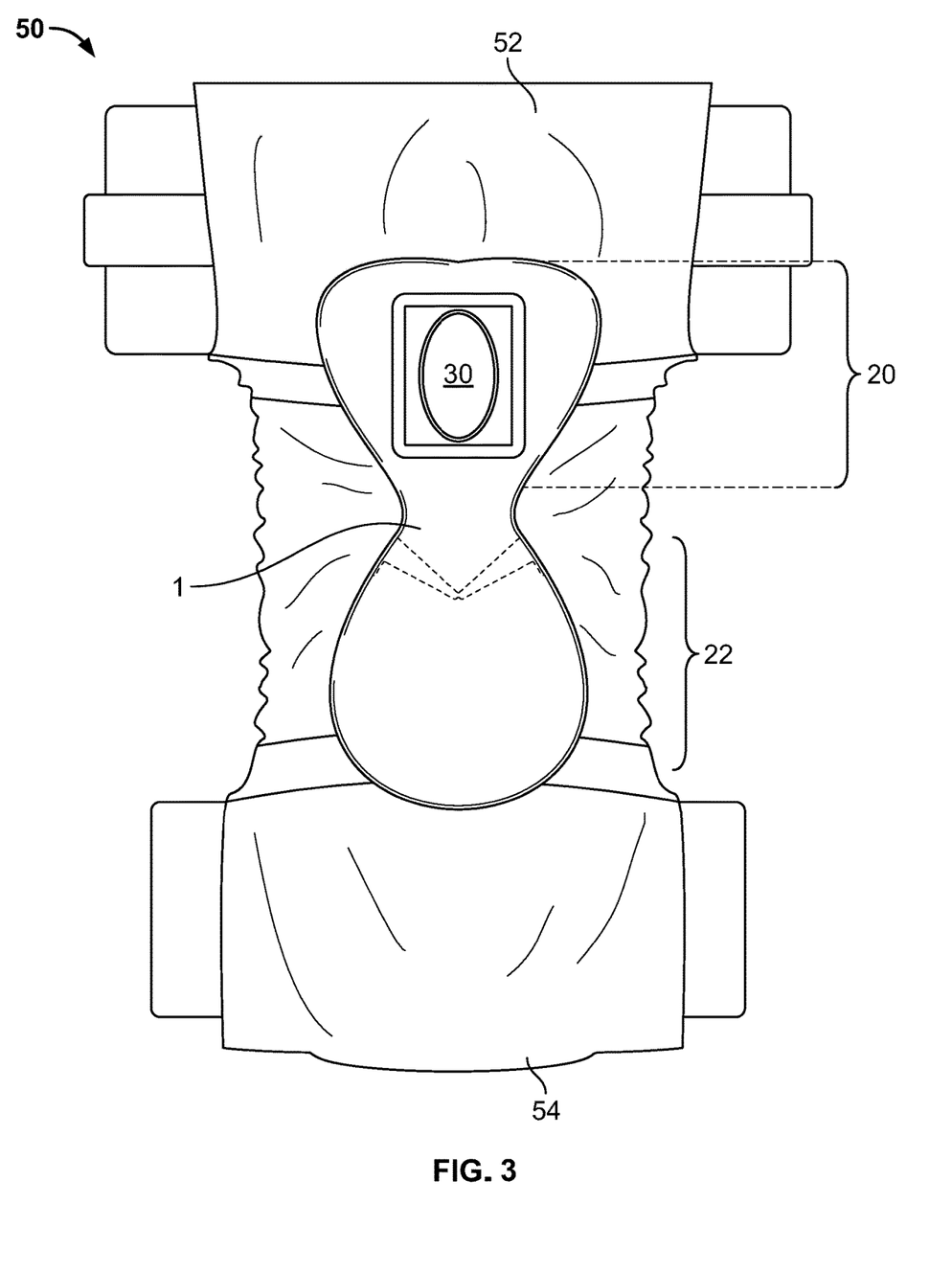
FIG. 3 illustrates a front view of the urine collection insert inserted into a diaper.

Referring to FIG. 3, a front view of the urine collection insert inserted into a diaper is shown.

The urine collection insert 1 is inserted into the diaper 50 with the collection section 20 near the diaper front 52, and the storage section 22 near the diaper rear 54. This aligns the opening 30 with the infant's genitals when the diaper is applied.

Figure 4:
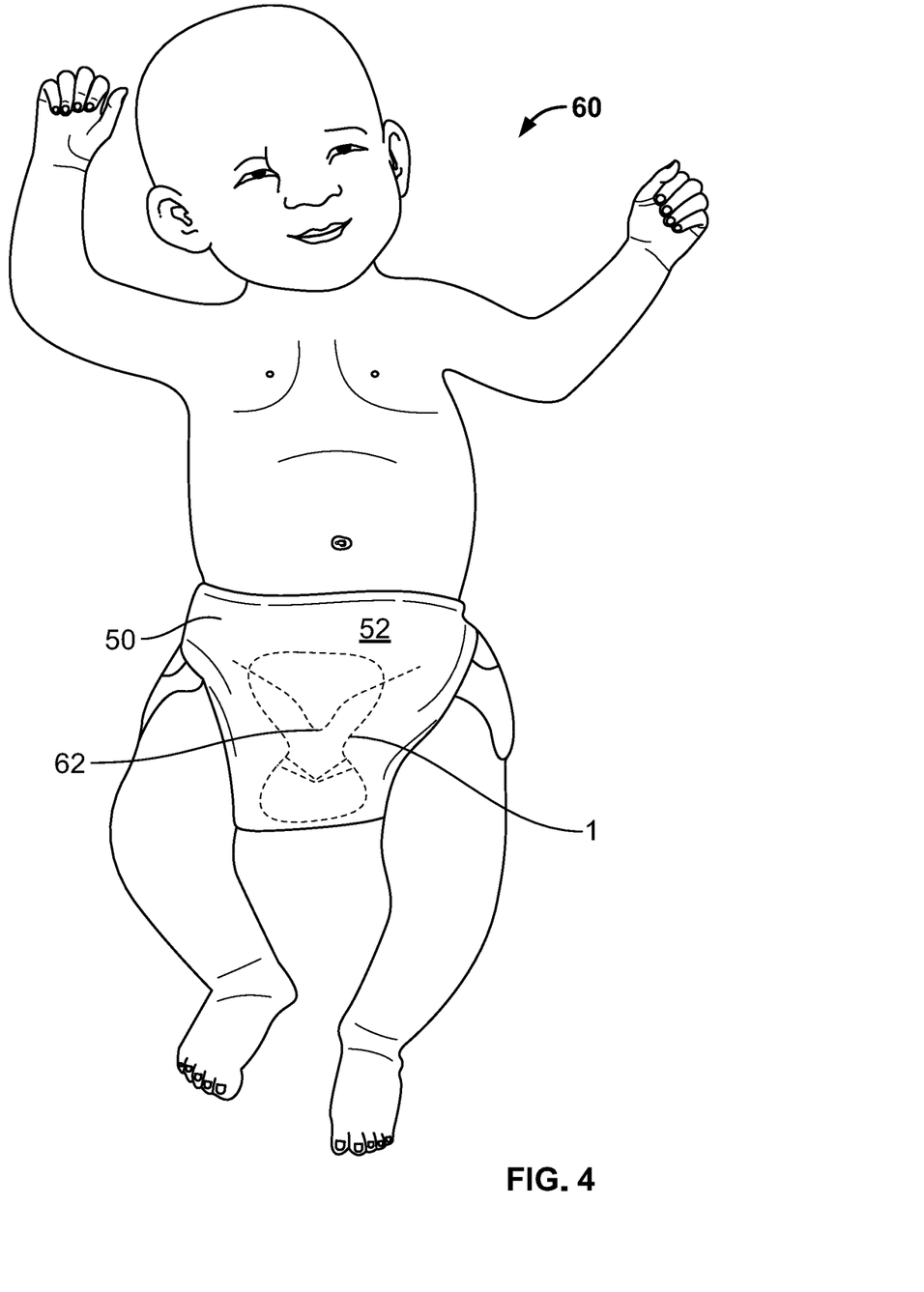
FIG. 4 illustrates a front view of the urine collection insert within a diaper, applied to an infant.

Referring to FIG. 4, a front view of the urine collection insert, within a diaper applied to an infant, is shown.

The genitals 62 of infant 60 align with the urine collection insert 1 in a manner that permits collection of urine 100 (See FIG. 1).

Figure 5:
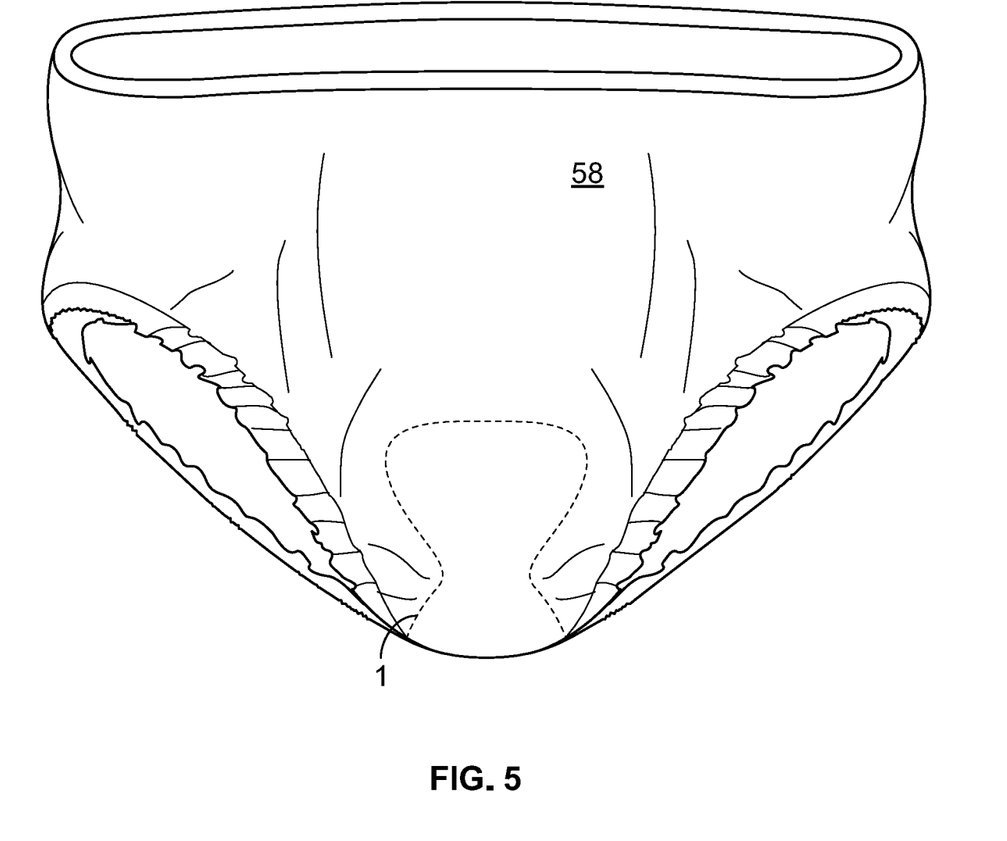
FIG. 5 illustrates a front view of the urine collection insert integrated into underwear.

Referring to FIG. 5, a front view of the urine collection insert integrated into underwear is shown.

In addition to being used as a stand-alone insert, the urine collection insert 1 may be integrated into underwear 58. This simplifies alignment and collection for children and adults who do not require the features of a diaper.

Figure 6:
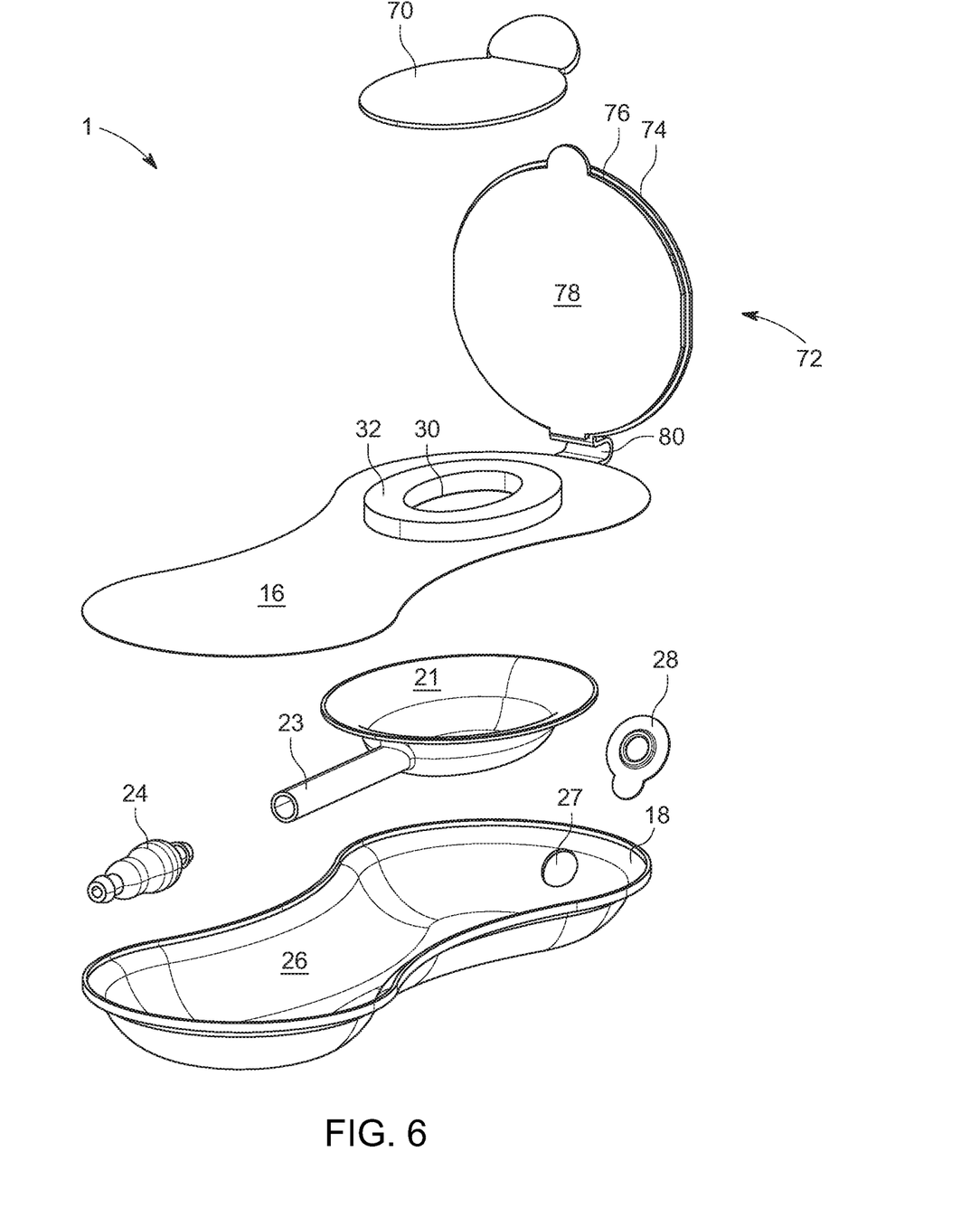
FIG. 6 illustrates a first exploded view of a second embodiment of the urine collection insert.
Figure 7:
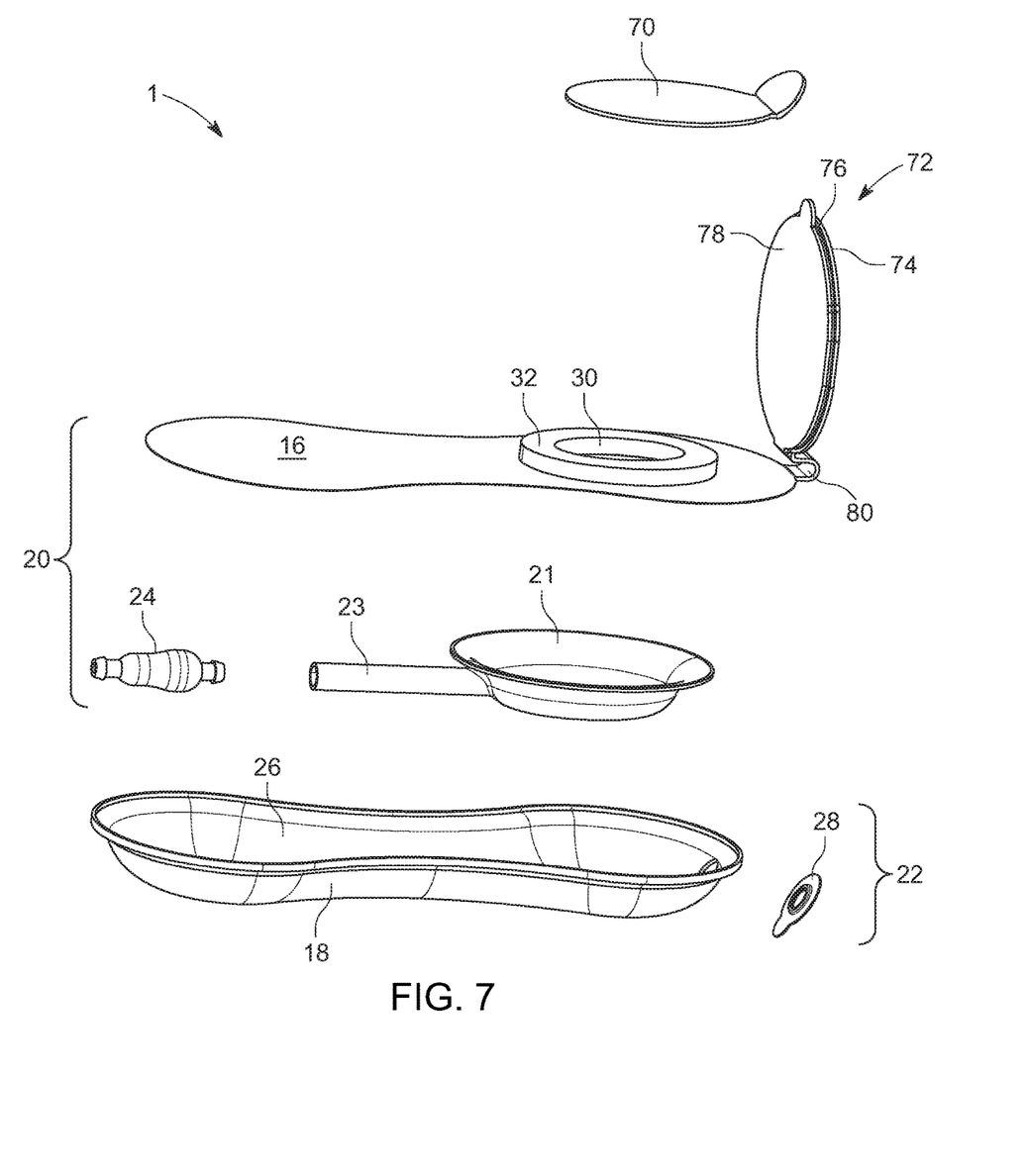
FIG. 7 illustrates a second exploded view of the second embodiment of the urine collection insert.

Referring to FIGS. 6 and 7, a first and second exploded view of a second embodiment of the urine collection insert are shown.

The second embodiment of the urine collection insert 1 is substantially formed from a base 16 and urine storage membrane 18.

For use, the opening cover 70 is removed from the perimeter seal 32, exposing the opening 30. The infant's genitals pass through the opening 30, or are placed near the opening 30, into which urine passes during use.

Within the space formed by the base 16 and urine storage membrane 18, also referred to as the reservoir 26, sits the pocket 21, which carries urine to the valve inlet 23, and through the one-way valve 24. Urine is held within the reservoir 26 by the drain cover 28, which is opened for drainage.

After sufficient urine is collected, the urine collection insert 1 needs to be sealed. The adhesive cover 78 is removed from the post-collection seal 72, exposing the adhesive 76. The post-collection seal 72 is then folded along hinge 80, covering the opening 30 and perimeter seal 32. The ID tag 74 is now prominently visible, and the urine collection insert 1 is ready for transport to the lab for testing.

In this embodiment, the collection section 20 and storage section 22 overlap, nesting within each other. In other embodiments the collection section 20 and storage section 22 are separate from each other.

Figure 8:
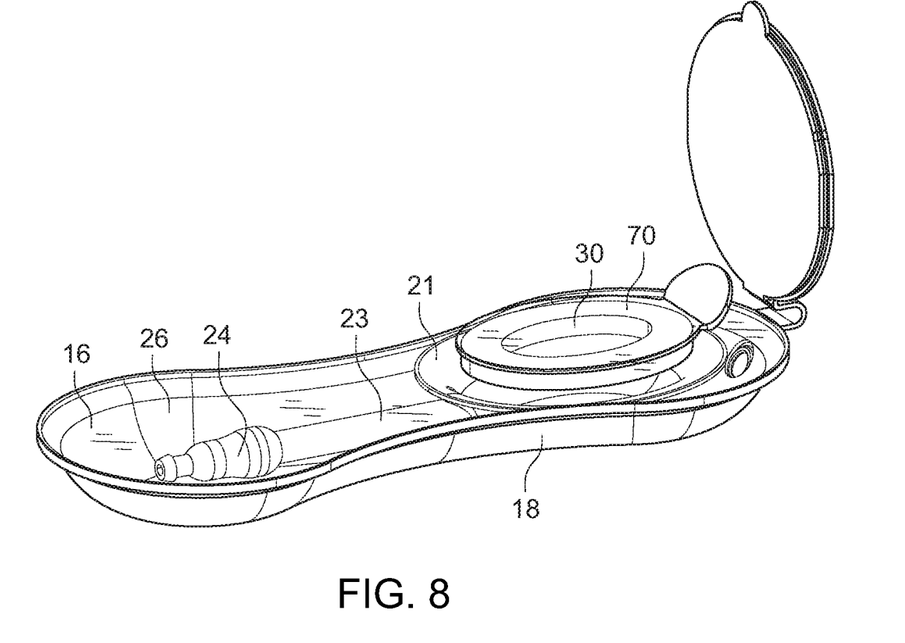
FIG. 8 illustrates an assembled, partially-transparent view, of the second embodiment of the urine collection insert.

Referring to FIG. 8, an assembled, partially-transparent view, of the second embodiment of the urine collection insert is shown.

The base 16 and opening cover 70 are shown as transparent to show the components within. The opening 30 leads to the pocket 21, connecting to the valve inlet 23 and one-way valve 24, which drawings into the reservoir 26.

Figure 9A:
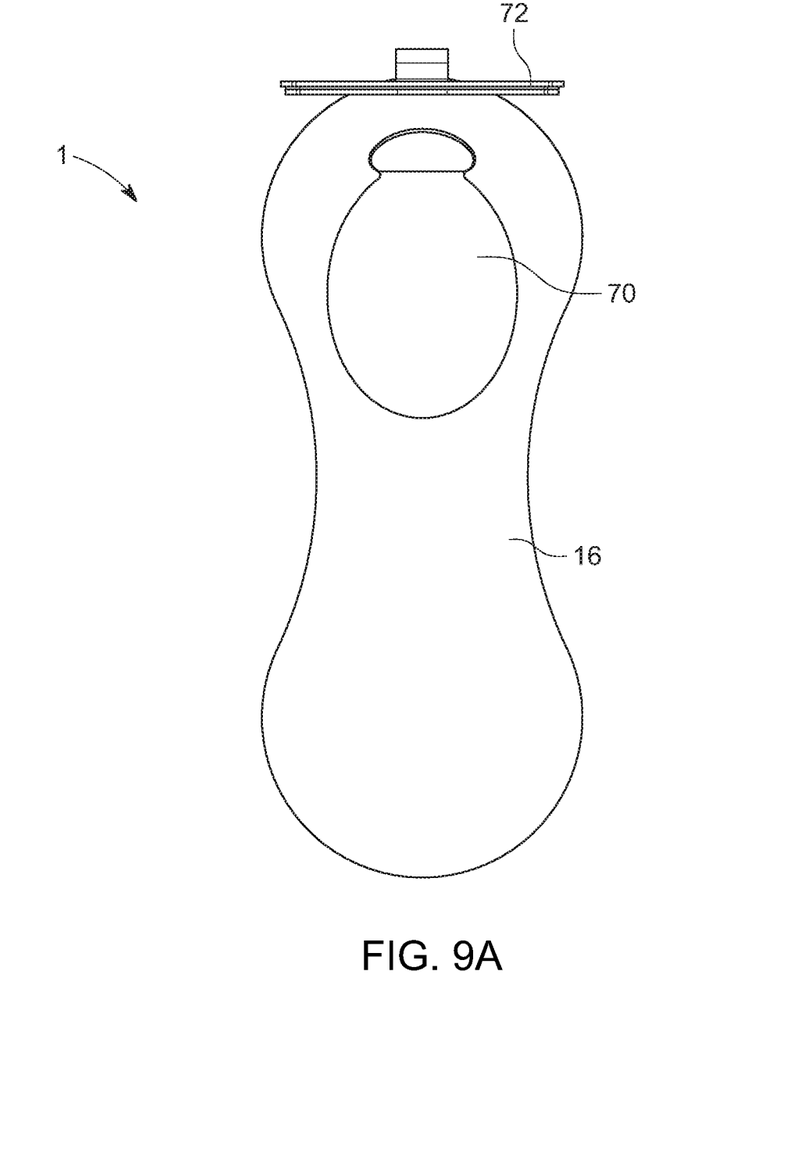
FIGS. 9A and 9B illustrate a top view and a bottom view of the second embodiment of the urine collection insert before use.
Figure 9B:
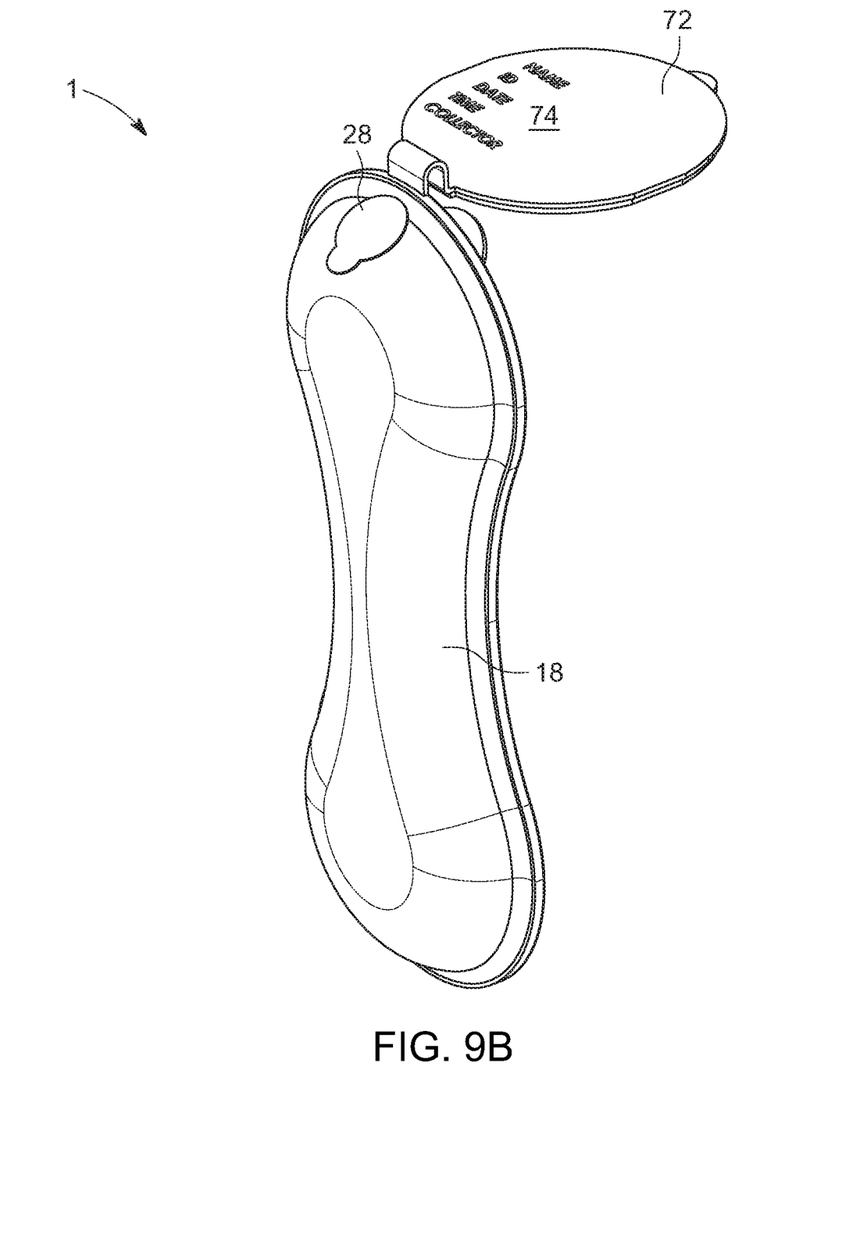

Referring to FIGS. 9A and 9B, a top view and a bottom view of the second embodiment of the urine collection insert before use is shown.

The urine collection insert 1 includes a base 16 and urine storage membrane 18. The opening cover 70 is removed for use, and later covered with the post-collection seal 72, which includes an ID tag 74. The drain cover 28 is removed for later urine drainage.

Figure 10A:
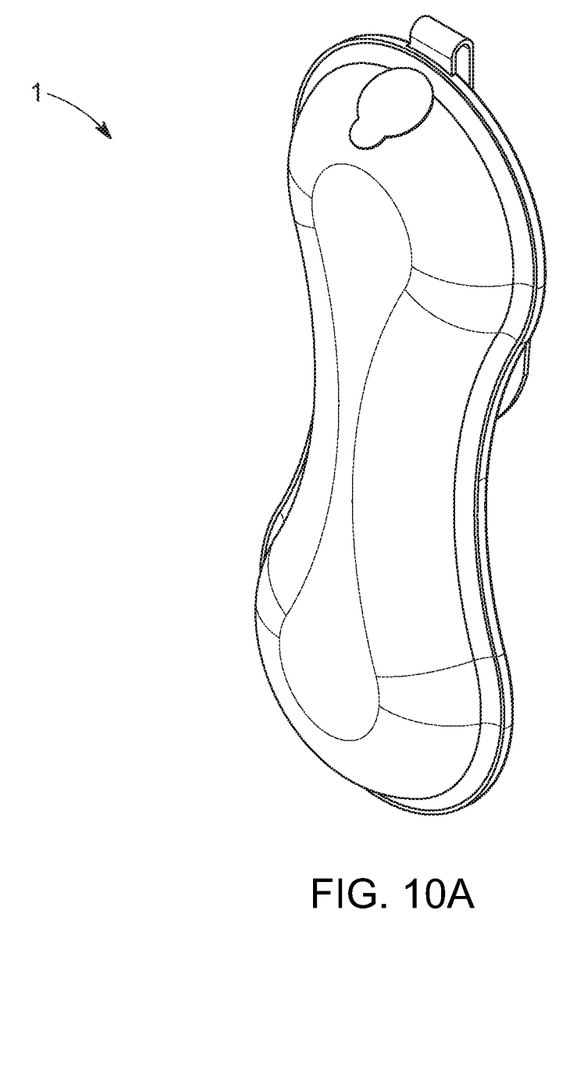
FIGS. 10A and 10B illustrate a top view and a bottom view of the second embodiment of the urine collection insert after sealing for transport.
Figure 10B:
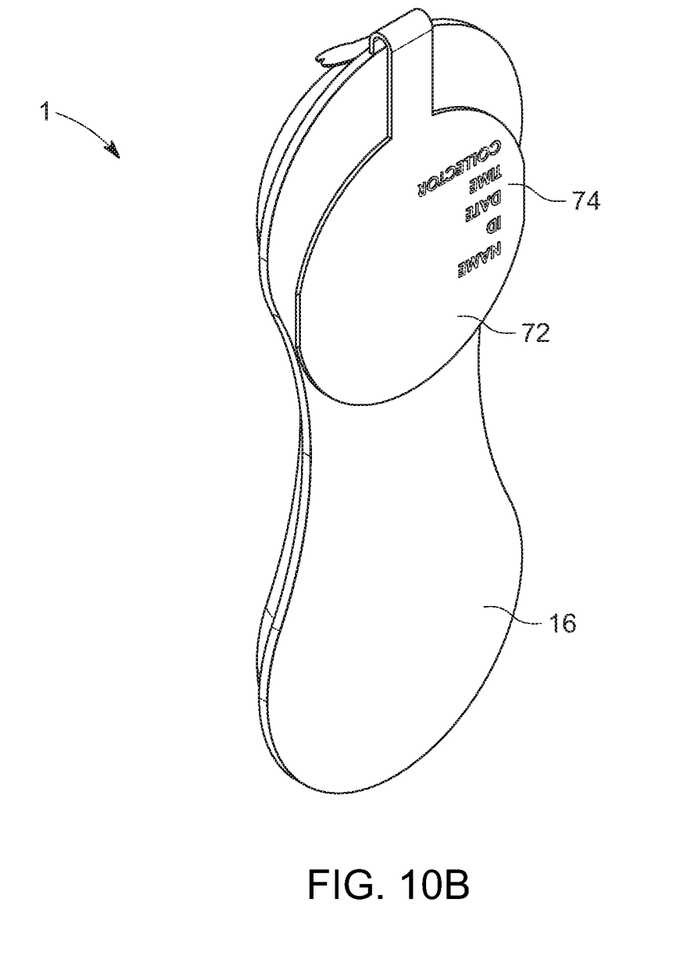

Referring to FIGS. 10A and 10B, a top view and a bottom view of the second embodiment after sealing for transport of the urine collection insert are shown.

The post-collection seal 72 is sealed to the base 16, orienting the ID tag 74 to make it easily visible.

Figure 11:
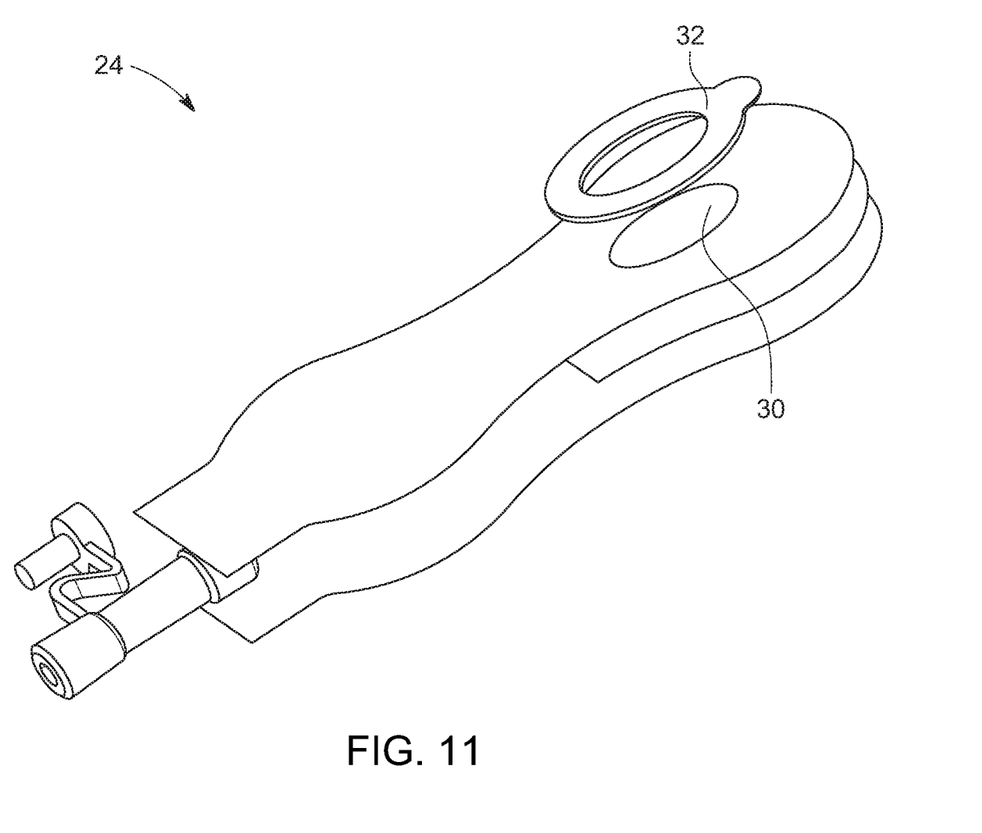
FIG. 11 illustrates an alternative embodiment of the one-way valve of the urine collection insert.

Referring to FIG. 11, an alternative embodiment of the one-way valve of the urine collection insert is shown.

The one-way valve 24 is shown with opening 30 and perimeter seal 32.

Figure 12:
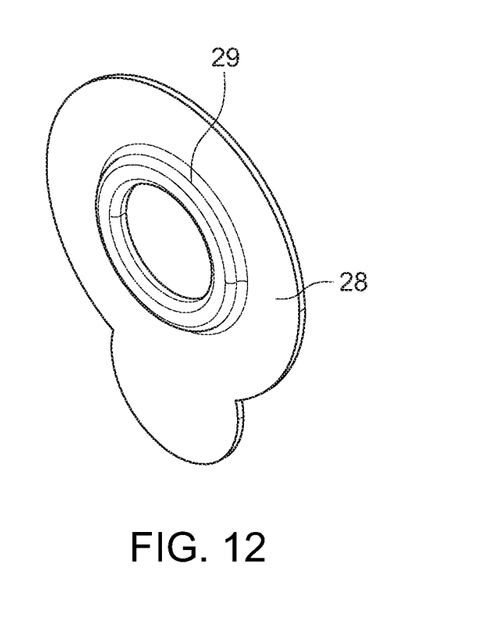
FIG. 12 illustrates a view of a drain cover of the urine collection insert.

Referring to FIG. 12, a view of a drain cover of the urine collection insert is shown.

The drain cover 28 includes a drain cover adhesive 29 that seals the drain cover 28 to the base 16 (see FIG. 7).

Figure 13:
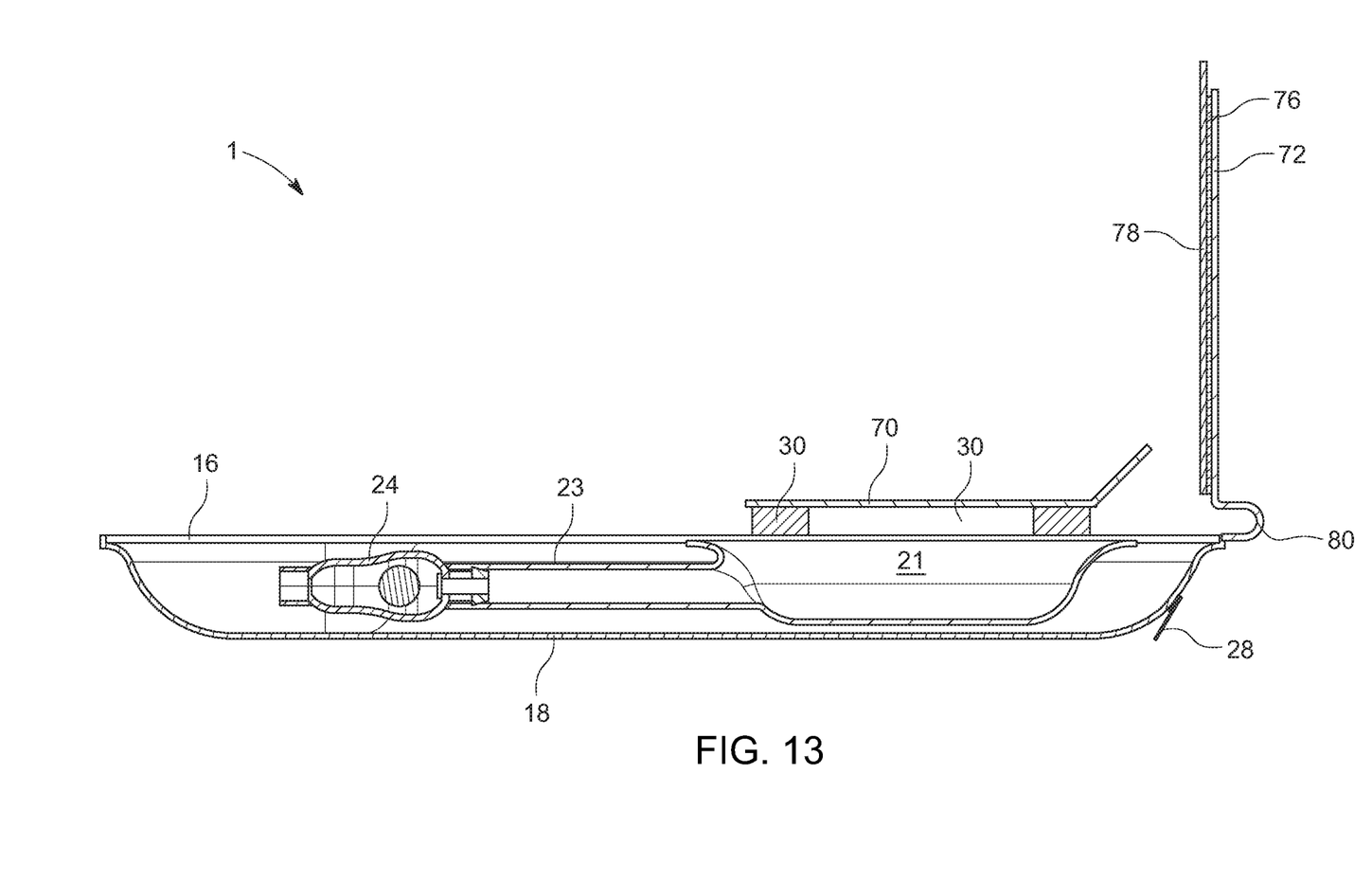
FIG. 13 illustrates a cross-sectional view of the second embodiment of the urine collection insert.

Referring to FIG. 13, a cross-sectional view of the second embodiment of the urine collection insert is shown.

The space created between the base 16 and urine storage membrane 18 includes the pocket 21, valve inlet 23, and one-way valve 24.

The one-way valve 24 is shown with a ball that permits flow in one direction, but excludes reverse flow.

The post-collection seal 72 includes adhesive 76 and adhesive cover 78, the post-collection seal 72 attached via a hinge 80.

The opening 30 and perimeter seal 32 are covered with the opening cover 70 until ready for use, maintaining a sterile environment within the urine collection insert 1.

Urine is released through the drain cover 28.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A urine collection device for use with an infant to collect urine, the device interfacing with genitals to exclude feces, the device comprising:
    an opening;
    a perimeter seal around the opening;
        the perimeter seal resting around the genitals of the infant during use, preventing feces from contaminating the urine;
    a one-way valve fluidly interfaced to the opening;
    a reservoir;
    a base creating a seal across a top of the reservoir;
    a post-collection seal for placement across the opening and the perimeter seal to prevent contaminants from entering the opening after use of the urine collection device;
        the post-collection seal attached to the base by a hinge;
            a first side of the post-collection seal including an identification tag;
            a second side of the post-collection seal including an adhesive layer with adhesive cover;
                the adhesive cover removed to expose the adhesive layer, the adhesive layer then used to affix the post-collection seal to the perimeter seal;
    whereby the post-collection seal applied after collection of urine is complete; and
    whereby urine from the infant flows through the opening, through the one-way valve, and into the reservoir, ready for testing.

2. The urine collection device of claim 1, further comprising:
    a removable opening cover placed across the opening to prevent contaminants from entering the opening before use of the urine collection device;
    the removable opening cover including a tab for a user to grip the removable opening cover during removal;
    whereby the removable opening cover must be fully removed before application of the urine collection device to the infant to create access to the reservoir.

* * * * *